US00PP13079P2

(12) United States Plant Patent
Shaw et al.

(10) Patent No.: US PP13,079 P2
(45) Date of Patent: Oct. 15, 2002

(54) STRAWBERRY PLANT NAMED 'CAMINO REAL'

(75) Inventors: Douglas V. Shaw, Davis; Kirk D. Larson, Irvine, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/778,100

(22) Filed: Feb. 7, 2001

(51) Int. Cl.[7] ..... A01H 5/00
(52) U.S. Cl. ..... Plt./208

(58) Field of Search ..... Plt./208

*Primary Examiner*—Bruce R. Campell
*Assistant Examiner*—Susan B. McCormick
(74) *Attorney, Agent, or Firm*—Burns, Doane, Swecker & Mathis, LLP

(57) ABSTRACT

A new and distinct short-day strawberry cultivar is provided. Attractive mostly symmetrical-conic fruit of very good quality typically is formed in a good yield. The fruit flavor is good and the fraction of non-marketable fruit tends to be low. The growth habit is very compact. Relatively small broad concave leaflets are formed that display semi-pointed serrations.

5 Drawing Sheets

FIELD OF THE INVENTION

A new and distinctive short-day type strawberry cultivar designated 'Camino Real' is provided that resulted from a cross performed in 1994 between advanced selections Cal 89.230-7 (non-patented in the United States) and Cal 90.253-3 (non-patented in the United States). The cultivar is botanically identified as *Fragaria×ananassa Duch.* The parentage of the new cultivar can be summarized as follows:

Cal 89.230-7×Cal 90.253-3.

'Camino Real' was first fruited at the University of California, Wolfskill Experimental Orchard, near Winters, Calif., U.S.A., in 1995, where it was selected, was originally designated Cal 94.3-11, and was propagated asexually by runners. The characteristics of the new cultivar have been found to be fully transmissible by such asexual propagation. Following selection and during testing the plant was designated 'C213', and subsequently has been named 'Camino Real' for introduction. Asexual propagules from this original source have been tested at the Watsonville Strawberry Research Facility, the South Coast Research and Extension Center of the University of California, and to a limited extent in grower test fields starting in 1996.

It was found that the new cultivar of the present invention exhibits the following combination of characteristics:

(a) Exhibits a very compact growth habit,
(b) Typically forms attractive mostly symmetrical-conic fruit of very good quality in a good yield, and
(c) Forms relatively small broad concave leaflets having semi-pointed serrations.

BRIEF DESCRIPTION OF THE PHOTOGRAPHS

The depicted plants and plant parts of the 'Camino Real' cultivar were grown at Watsonville, Calif., U.S.A.

Figure 1:
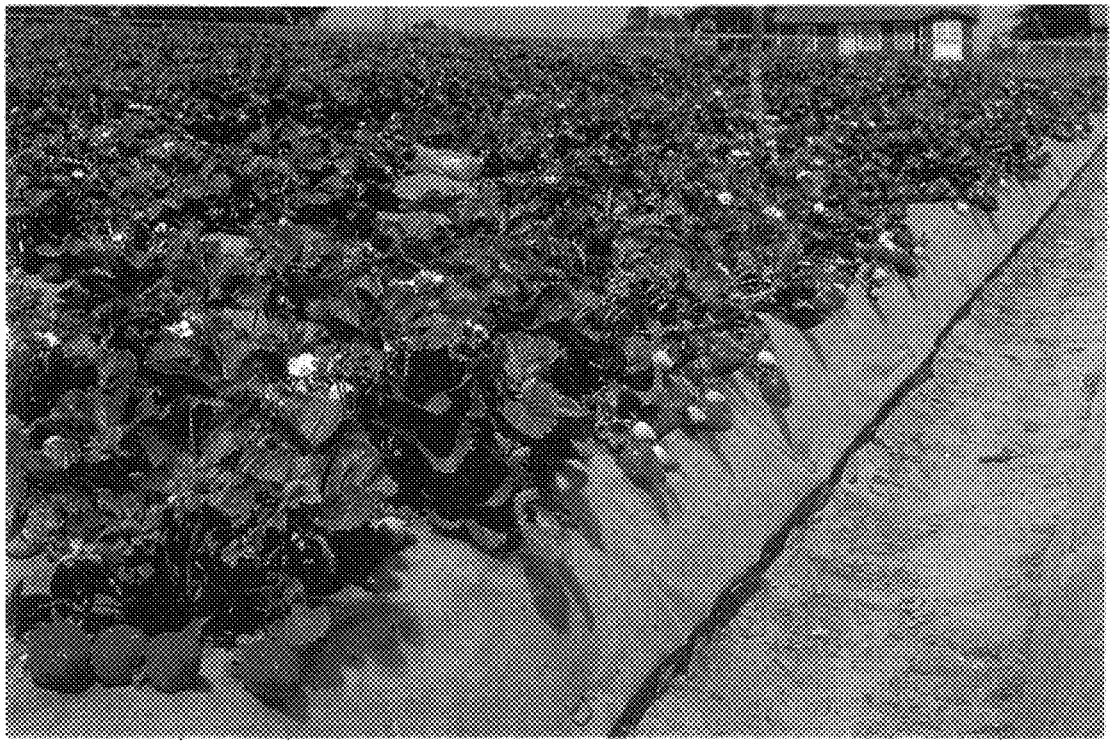
Figure 2:
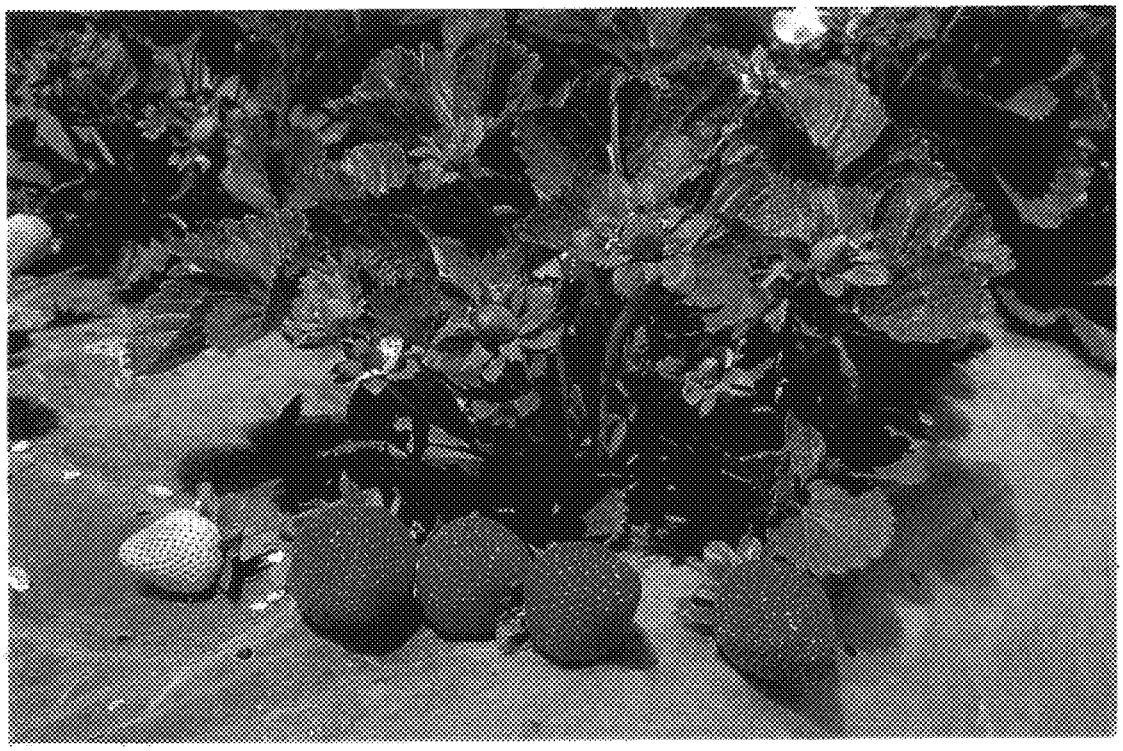
Figure 3:
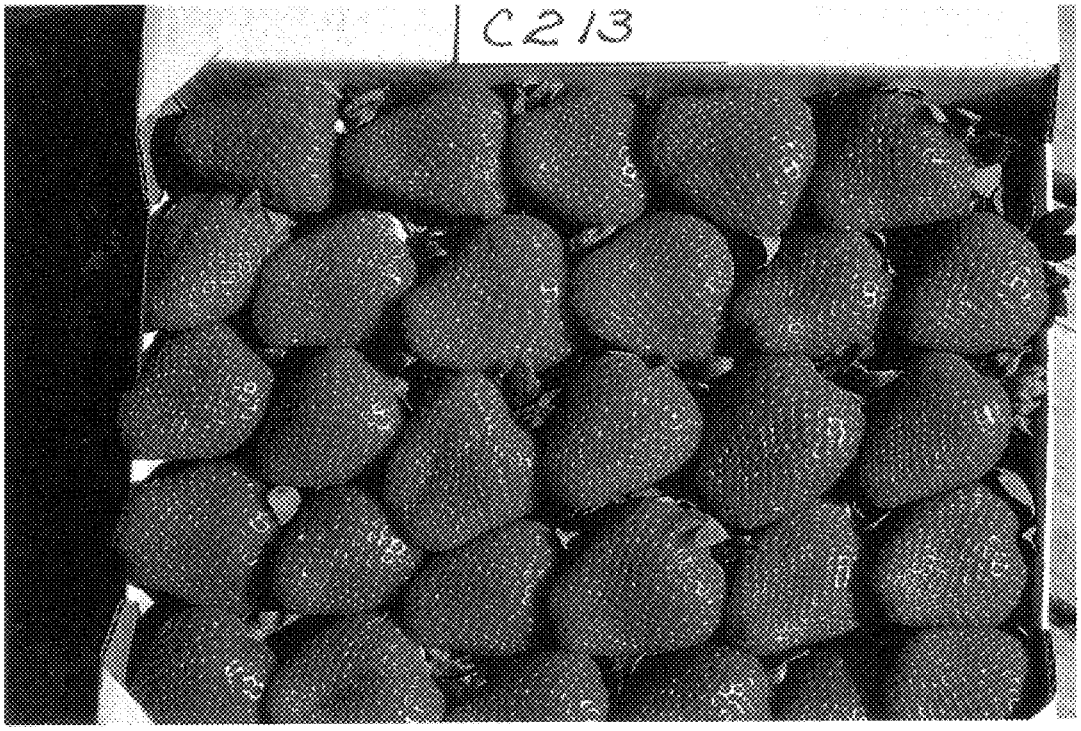
Figure 4:
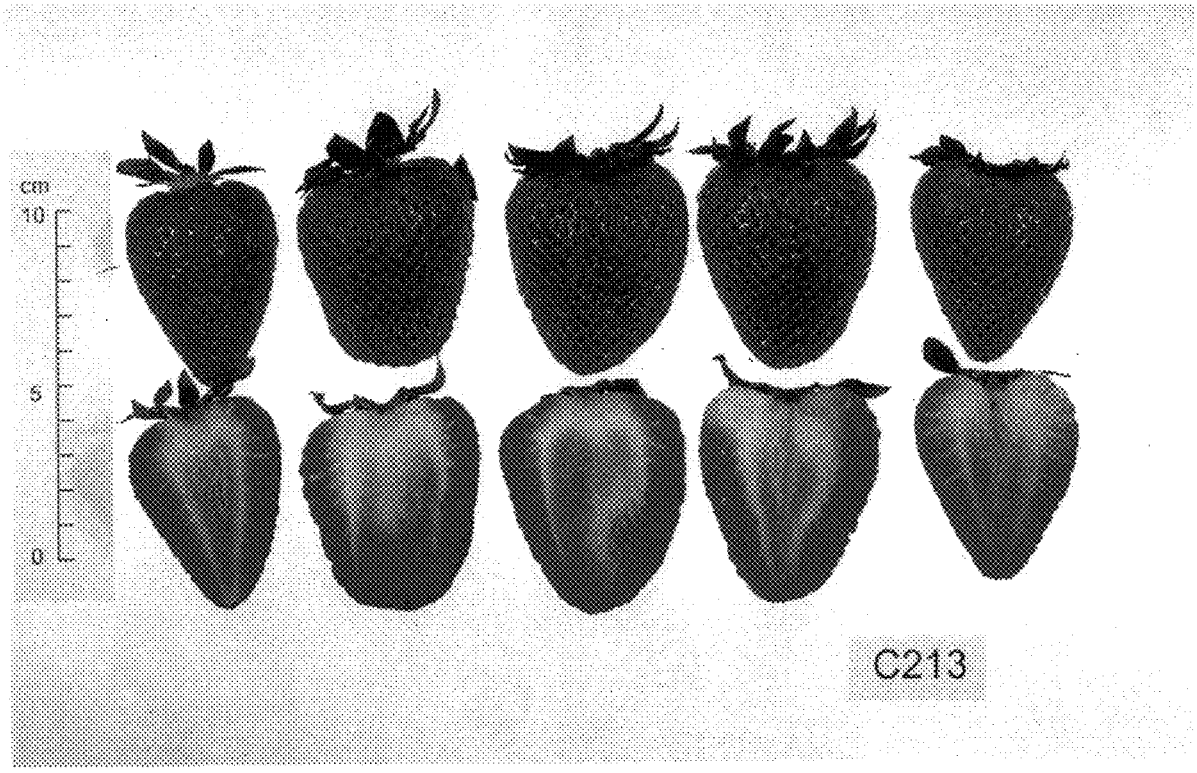
Figure 5:
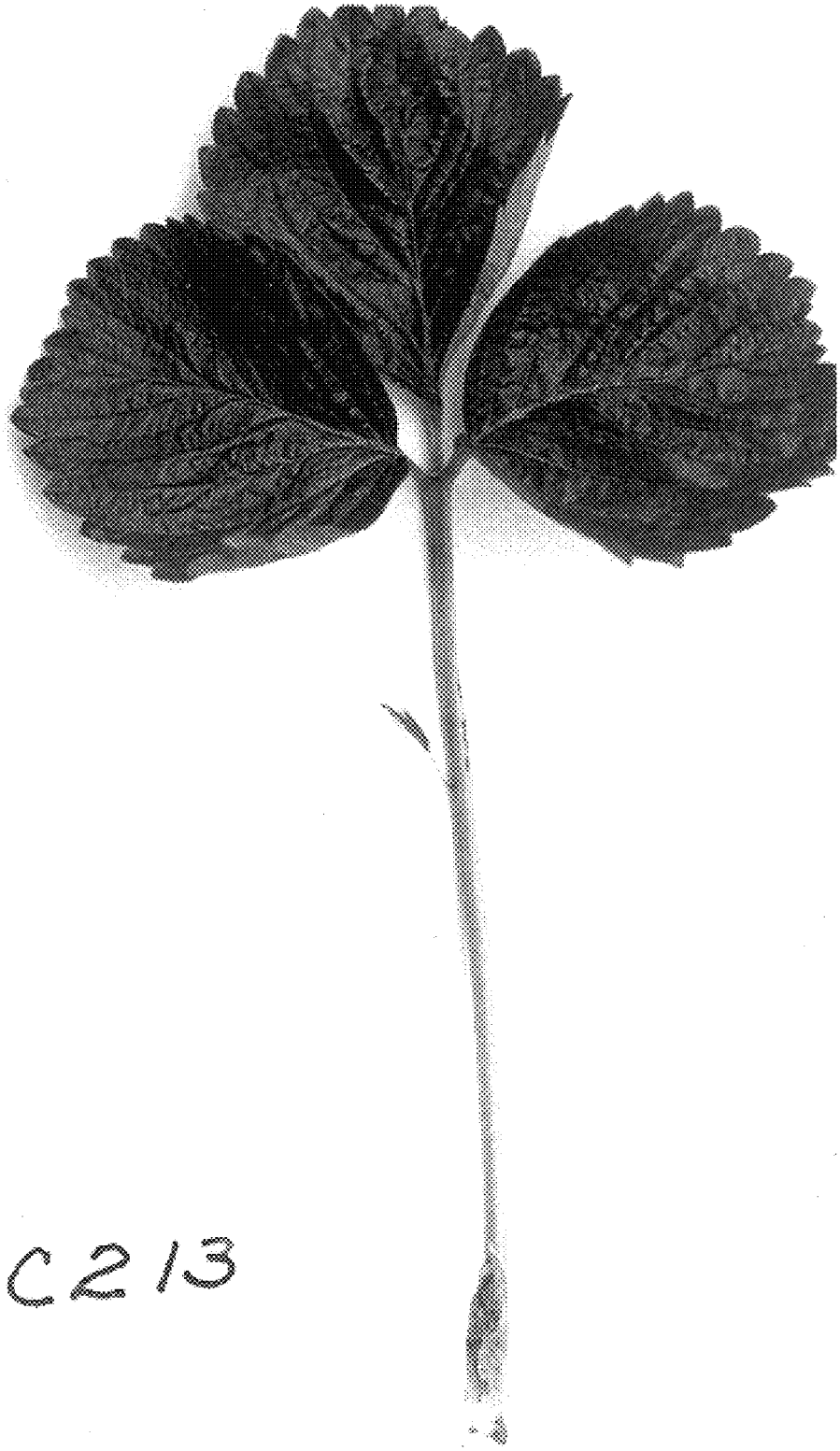

FIG. 1—shows rows of typical fruiting plants during early May, 2000;

FIG. 2—shows a close view of a representative individual fruiting plant during early May, 2000;

FIG. 3—shows a one-half crate of representative fruit during early May, 2000;

FIG. 4—shows representative mature fruit externally on the upper row and internally on the lower row with dimensions in centimeters being shown at the left; and FIG. 5—shows a typical mature leaf during late spring.

DETAILED DESCRIPTION

'Camino Real' as other short-day strawberry cultivars produces fruit over an extended period when treated appropriately in arid, subtropical climates. The production pattern for 'Camino Real' is similar to that of the 'Camarosa' cultivar U.S. Plant Pat. No. 8,708), although it is somewhat later to initiate fruiting with most cultural treatments. 'Camino Real' will be of special interest for winter plantings where the 'Camarosa' cultivar has been successful, and in summer plantings where the 'Pajaro' cultivar (U.S. Plant Pat. No. 4,538) and the 'Chandler' cultivar (U.S. Plant Pat. No. 5,262) have been successful.

Plants and Foliage

Fruiting plants of 'Camino Real' are smaller and more compact, more open, more erect, and less vigorous than plants of the 'Camarosa' cultivar. The 'Camino Real' plants are more compact but less erect than those of the 'Gaviota' cultivar (U.S. Plant Pat. No. 10,461). Comparative statistics for foliar characters near mid-season are given for the three cultivars in Table 1 that follows. Individual leaflets of 'Camino Real' are smaller than those of the 'Gaviota' and 'Camarosa' cultivars, and are somewhat more rounded than those of the 'Camarosa' cultivar. Leaves (including petioles) are similar in length to those of the 'Gaviota' cultivar, but are much broader. The leaves of 'Camino Real' are shorter and broader than those of the 'Camarosa' cultivar. Petioles are similar in thickness to those of 'Gaviota' cultivar. Leaves on vigorous plants of 'Camino Real' occasionally have 4 or 5 leaflets. 'Camino Real' has a consistently concave leaf form, generally much more concave than leaves of the 'Gaviota' and 'Camarosa' cultivars, and has more and usually more pointed serrations than these comparison cultivars. Plant height and width values were obtained for established plants growing at Watsonville, Calif. that were established on October 23rd and were measured on January 21st. This is the industry standard for planting these cultivars at this location. The typical length and color of the stipule is provided. The stipule color varies somewhat depending on age and stage of development. Individual stipules commonly display a green interior and reddish margins. The stipules are substantially the same for all three varieties. Strawberry plants do not commonly produce stolons during the fruiting period in annual planted systems such as those used in California. The stolon information included in Table 1 is estimated from the initial stolon production in a foundation nursery located near Redding, Calif.

TABLE 1

| | Cultivar | | |
|---|---|---|---|
| Foliar Character | 'Camarosa' | 'Gaviota' | 'Camino Real' |
| Plant height (mm) | | | |
| mean | 56 | 54 | 62 |
| range | 40–70 | 50–50 | 50–70 |
| Plant spread (mm) | | | |
| mean | 167 | 143 | 193 |
| range | 150–200 | 130–155 | 165–220 |
| Mid-Tier Leaflet | | | |
| Length (mm) | | | |
| mean | 91 | 95 | 81 |
| range | 80 to 100 | 83 to 109 | 64 to 90 |
| Width (mm) | | | |
| mean | 83 | 95 | 82 |
| range | 68 to 104 | 71 to 105 | 62 to 95 |
| Mid-Tier Leaf | | | |
| Length (mm) | | | |
| mean | 313 | 254 | 252 |
| range | 256 to 426 | 201 to 314 | 199 to 314 |
| Width (mm) | | | |
| mean | 161 | 182 | 150 |
| range | 130 to 183 | 146 to 205 | 125 to 173 |
| Leaf components | | | |
| Petiole length (mm) | | | |
| mean | 209 | 168 | 170 |
| range | 171–285 | 133–208 | 135–212 |
| Petiole diameter (mm) | | | |
| mean | 3.0 | 3.2 | 3.1 |
| range | 2.9–3.1 | 3.1–3.4 | 2.9–3.3 |
| Petiolule length (mm) | | | |
| mean | 11 | 11 | 11 |
| range | 9–16 | 9–14 | 9–14 |
| Number of Leaflets/Leaf | 3 | 3 | 3, rarely 4 or 5 |
| Leaf Convexity | flat-convex, most are slightly concave | most are concave, some flat | very concave |
| Serrations | | | |
| number/leaf (mean) | 19.4 | 17.8 | 17.8 |
| range | 18–21 | 16–19 | 17–20 |
| shape | rounded, some semi-pointed | rounded to semi-pointed | semi-pointed |
| Leaf Pubescence | light-moderate | light-moderate | light |

TABLE 1-continued

| | Cultivar | | |
|---|---|---|---|
| Foliar Character | 'Camarosa' | 'Gaviota' | 'Camino Real' |
| Petiole Pubescence | | | |
| density | moderate to heavy | heavy | moderate |
| direction | perpendicular to acropetal | perpendicular | perpendicular |
| Petiole color (Munsell) | 2.5 GY 5/5 | 2.5 GY 6/8 | 2.5 GY 6/8 |
| Stipule length (mm) | | | |
| mean | 22 | 21.8 | 26.2 |
| range | 20–23 | 21–23 | 23–30 |
| Stipule color | | | |
| core | 2.5 GY 6/8 | 2.5 GY 6/8 | 2.5 GY 6/8 |
| margins | 2.5 R 6/11 | 2.5 R 6/11 | 2.5 R 6/11 |
| Stolons per nursery mother plant | 215 | 194 | 184 |
| Venation pattern | pinnate | pinnate | pinnate |
| Color (Munsell) | 2.5 GY 6/8 | 2.5 GY 6/8 | 2.5 GY 6/8 |

The adaxial (upper) surfaces of leaves of 'Camino Real' are darker than those of the 'Gaviota' cultivar and the 'Camarosa' cultivar, and the abaxial (lower) leaf surface colors are similar. See Table 2 that follows.

TABLE 2

| | Cultivar | | |
|---|---|---|---|
| Color Character | 'Camarosa' | 'Gaviota' | 'Camino Real' |
| Leaf Color (CIELAB)* | | | |
| Adaxial | | | |
| L* | | | |
| mean | 32.3 | 29.0 | 27.4 |
| range | 30.8 to 34.6 | 27.4 to 30.0 | 26.1 to 28.5 |
| a* | | | |
| mean | −7.0 | −7.0 | −6.4 |
| range | −4.8 to −8.2 | −6.1 to −7.7 | −5.3 to −8.0 |
| b* | | | |
| mean | 14.0 | 11.5 | 11.1 |
| range | 9.4 to 18.4 | 9.7 to 13.7 | 9.4 to 14.3 |
| Munsell | 5GY 4/3 | 5GY 4/3 | 5GY 4/3 |
| Abaxial | | | |
| L* | | | |
| mean | 46.1 | 47.5 | 45.7 |
| range | 43.9 to 49.2 | 46.4 to 48.7 | 44.0 to 47.5 |
| a* | | | |
| mean | −7.6 | −7.6 | −7.5 |
| range | −6.8 to −8.0 | −6.7 to −8.5 | −6.6 to −8.3 |
| b* | | | |
| mean | 21.8 | 20.4 | 19.8 |
| range | 20.1 to 25.0 | 17.2 to 24.5 | 18.4 to 20.7 |
| Munsell | 2.5GY 5/5 | 2.5GY 5/5 | 2.5GY 4/3 |

*CIELAB is the abbreviation of the international color system known as "Commission Internationale De L' Eclairage" 1978. For recommendations concerning uniform color spaces, color difference equations, and psychometric color terms see Supplement No. 2 of CIE Publication No. 15, Paris.

Isozymes in Leaf Extracts

'Camino Real' has been classified for three isozyme systems using Starch Gel Electrophoresis: Phosophoglucoisomerase (PGI), Leucine Aminopeptidase (LAP), and Phosphoglucomutase (PGM). It is distinguishable from the 'Gaviota' and 'Camarosa' cultivars using this methodology. See Table 3 that follows.

TABLE 3

| | Cultivar | | |
|---|---|---|---|
| Locus | 'Camarosa' | 'Gaviota' | 'Camino Real' |
| PGI | A2 | A2 | A2 |
| LAP | B3 | B3 | B3 |
| PGM | C1 | C1 | C3 |

For electrophoretic procedures see: *J. Amer. Soc. Hort. Sci.* 106:684 to 687.

Disease and Pest Reactions

'Camino Real' is moderately susceptible to common leaf spot (*Ramularia tulasnei*) and somewhat sensitive to powdery mildew (*Sphaerotheca macularis*). It is quite resistant to Verticillium wilt (*Verticillium dahliae*) and Phytophthora crown rot (*Phytophthora cactorum*), and relatively resistant to Anthracnose crown rot (*Colletotrichum acutatum*). When treated properly, it has tolerance to two-spotted spidermites (*Tetranychus urticae*) equal or greater than 'Gaviota' and 'Camarosa'. 'Camino Real' is tolerant to strawberry viruses encountered in California.

Flowering, Fruiting, Fruit and Production Characteristics

Comparative statistics for flower and fruit characters near mid-season are given for 'Camarosa', 'Gaviota' and 'Camino Real' in Table 4 that follows. The primary flowers for 'Camino Real' are similar in size to those of the 'Gaviota' and 'Camarosa' cultivars. The petals for all three cultivars are white on both surfaces. The petal apex for all three cultivars is flat across the top with slightly rounded edges to slightly rounded across the top. The sepals are somewhat larger than those of the 'Gaviota' cultivar and are similar to those of the 'Camarosa' cultivar. The number of sepals equals the number of petals for all three cultivars. The calyx for 'Camino Real' varies from slightly indented to slightly necked, and each primary flower has 5 to 8 petals. The fruit shape for 'Camino Real' can vary but is typically rounded or symmetrical conic, and is easily distinguishable from that of the 'Camarosa' cultivar that is shortened flat conic. 'Camino Real' commonly has a greater proportion of symmetrical fruit than the 'Gaviota' cultivar. The fruit color information included in Table 4 was obtained using a reflectance spectrophotometer that integrates color over a 1.5 cm diameter circle. As indicated in FIG. 4, the internal fruit coloration is variable over a wide range and is lighter in the center than at the margin. This wide color variation is present in almost all strawberry cultivars. Achenes vary from yellow to dark red, and are generally even with the fruit surface or slightly indented. The pedicel information included in Table 4 was obtained on Jan. 21, 2002.

TABLE 4

| | Cultivar | | |
|---|---|---|---|
| Character | 'Camarosa' | 'Gaviota' | 'Camino Real' |
| Number of Petals | | | |
| mean | 6.3 | 5.9 | 5.8 |
| range | 5 to 8 | 5 to 8 | 5 to 8 |
| Petal shape | | | |
| apex | truncate to slightly obtuse | truncate to slightly obtuse | truncate to slightly obtuse |
| base | attenuate | attenuate | attenuate |
| margin | entire | entire | entire |
| Petal length (mm) | | | |
| mean | 14.4 | 14.4 | 17.4 |
| range | 14–15 | 13–15 | 16–19 |
| Petal width (mm) | | | |
| mean | 14.2 | 15.7 | 17.4 |
| range | 14–15 | 14–17 | 17–18 |
| Flower Position (relative to foliage) | mostly even some exposed | exposed | exposed |
| Calyx Diam. (mm) | | | |
| mean | 48.1 | 41.7 | 47.1 |
| range | 32 to 58 | 30 to 58 | 37 to 57 |
| Corolla Diam. (mm) | | | |
| mean | 35.6 | 37.9 | 26.8 |
| range | 30 to 47 | 32 to 48 | 32 to 42 |
| Sepal length (mm) | | | |
| mean | 17.8 | 16.2 | 19.8 |
| range | 17–20 | 15–17 | 19–20 |
| Sepal width (mm) | | | |
| mean | 6.4 | 9.6 | 6–8 |
| range | 6–7 | 9–11 | 6–7 |
| Sepal color (Munsell) | 7.5 GY 4/4 | 5 GY 4/3 | 5 GY 4/3 |
| Pedicel length (mm) | | | |
| mean | 93.2 | 72.8 | 76.0 |
| range | 85–112 | 62–87 | 72–80 |
| Pedicel diameter (mm) | | | |
| mean | 2.4 | 2.6 | 2.8 |
| range | 2.2–2.5 | 2.5–2.9 | 2.7–2.9 |
| Pedicel color (Munsell) | 5 GY 6/8 | 2.5 GY 6/8 | 5 GY 6/8 |
| Fruit Shape | | | |
| Fruit length (mm) | | | |
| mean | 54 | 54 | 56 |
| range | 42–63 | 45–70 | 48–68 |
| Fruit width (mm) | | | |
| mean | 49 | 44 | 50 |
| range | 39–72 | 37–51 | 43–62 |
| length/width | | | |
| ratio | 1.13 | 1.22 | 1.14 |
| range | 0.61 to 1.51 | 1.02 to 1.45 | 0.92 to 1.28 |
| subjective | short flat conic | mostly rounded conic, some flat conic | mostly symmetrical conic, some flat conic |

TABLE 4-continued

| Character | Cultivar 'Camarosa' | 'Gaviota' | 'Camino Real' |
|---|---|---|---|
| Calyx Position | even to slightly necked | even to slightly indented | even to slightly indented |
| Seed Position | even to slightly indented | even | even |

External and internal fruit color for 'Camino Real' is darker than that of the 'Camarosa' cultivar, and slightly darker than that of the 'Gaviota' cultivar. See Table 5 that follows where CIELAB fruit color information is presented.

TABLE 5

| | Cultivar 'Camarosa' | 'Gaviota' | 'Camino Real' |
|---|---|---|---|
| External | | | |
| L* | | | |
| mean | 23.3 | 22.4 | 20.1 |
| range | 20.7 to 27.0 | 20.3 to 24.5 | 15.6 to 22.9 |
| a* | | | |
| mean | 26.6 | 28.2 | 26.3 |
| range | 21.6 to 29.5 | 25.3 to 31.4 | 21.6 to 29.4 |
| b* | | | |
| mean | 12.8 | 14.8 | 13.6 |
| range | 9.9 to 14.6 | 12.0 to 17.7 | 7.8 to 20.3 |
| Munsell | 2.5R 3/7 | 5R 3/7 | 5R 3/7 |
| Internal | | | |
| L* | | | |
| mean | 44.0 | 48.1 | 40.2 |
| range | 40.7 to 46.9 | 44.3 to 53.9 | 26.3 to 45.4 |
| a* | | | |
| mean | 41.4 | 37.2 | 39.2 |
| range | 35.0 to 45.1 | 26.1 to 41.3 | 31.8 to 43.6 |
| b* | | | |
| mean | 29.9 | 28.6 | 28.8 |
| range | 24.1 to 35.3 | 19.9 to 32.6 | 19.8 to 35.5 |
| Munsell | 5R 4/12 | 5R 5/13 | 5R 5/13 |

Performance

'Camino Real' has been tested under a variety of cultural regimes, and optimal performance is obtained when nursery treatments and nutritional programs similar to those used with the 'Gaviota' and 'Camarosa' cultivars are employed. In general, 'Camino Real' is less adapted to very early season planting but less sensitive to excess chilling than the 'Camarosa' cultivar. 'Camino Real' retains excellent fruit quality in summer planting systems.

When treated with appropriate planting regimes, 'Camino Real' has larger fruit and produces greater individual-plant yields than the 'Gaviota' or 'Camarosa' cultivars. 'Camino Real' is intermediate to the 'Gaviota' and 'Camarosa' cultivars in its production pattern. It is somewhat later to initiate production than the 'Camarosa' cultivar, with conventional winter planting in central California but has earlier average production than the 'Gaviota' cultivar. Commercial appearance ratings have been better than those for the 'Gaviota' and 'Camarosa' cultivars and trials conducted at Santa Maria, Calif., U.S.A. in 1998 to 1999 have indicated that the fraction of non-marketable fruit is approximately one-half that produced by the 'Camarosa' cultivar. Fruit for 'Camino Real' is substantially firmer than the fruit of the 'Gaviota' cultivar, and is similar in firmness to that of the 'Camarosa' cultivar. Subjectively, the 'Camino Real' fruit has very good flavor. The fruit will be outstanding for both the fresh market and for processing, and will be useful for home garden purposes as well. See the comparative data presented in Table 6 that follows. There information is provided for plants that were evaluated during 1998 and 1999 at the Watsonville, Calif., U.S.A., Research Faculty of the University of California. Such plants had been asexually reproduced by the use of runners at Macdoel, Calif., U.S.A., were harvested on October $15^{th}$, and were subjected to supplemental storage for approximately 7 to 10 days prior to being transplanted. The test planting consisted of 52 inch two-row beds, 17,300 plants/acre. Harvest was initiated in early April and continued through the last week of August.

TABLE 6

| Cultivar | Yield (g/plant) | Appearance Score | Size (g/fruit) | Firmness |
|---|---|---|---|---|
| 'Camarosa' | 1,783 | 3.3 | 27.2 | 7.7 |
| 'Gaviota' | 1,437 | 3.5 | 27.8 | 7.1 |
| 'Camino Real' | 1,813 | 3.8 | 31.1 | 7.6 |

'Camino Real' has not been observed under all possible environmental conditions to date. Accordingly, it is possible that the phenotype may vary somewhat with variations in the environment.

We claim:

1. A new and distinct short-day strawberry plant cultivar that exhibits the following combination of characteristics:

(a) Exhibits a very compact growth habit, (b) Typically forms attractive mostly symmetrical-conic fruit of very good quality in a good yield, and (c) Forms relatively small broad concave leaflets having semi-pointed serrations;

substantially as illustrated and described.

* * * * *